United States Patent
Matsumura (10) Patent No.: US 10,827,933 B2
(45) Date of Patent: Nov. 10, 2020

(54) SENSOR, AND PATIENT MONITORING SYSTEM

(71) Applicant: NIHON KOHDEN CORPORATION, Tokyo (JP)

(72) Inventor: Fumiyuki Matsumura, Tokorozawa (JP)

(73) Assignee: NIHON KOHDEN CORPORATION, Tokyo (JP)

( * ) Notice: Subject to any disclaimer, the term of this patent is extended or adjusted under 35 U.S.C. 154(b) by 0 days.

(21) Appl. No.: 16/438,773

(22) Filed: Jun. 12, 2019

(65) Prior Publication Data

US 2019/0380590 A1 Dec. 19, 2019

(30) Foreign Application Priority Data

Jun. 13, 2018 (JP) .................. 2018-112861

(51) Int. Cl.
| | |
|---|---|
| *A61B 5/0205* | (2006.01) |
| *A61B 5/00* | (2006.01) |
| *A61B 5/021* | (2006.01) |
| *A61B 5/0476* | (2006.01) |
| *A61B 5/11* | (2006.01) |

(52) U.S. Cl.
CPC .......... *A61B 5/0205* (2013.01); *A61B 5/0008* (2013.01); *A61B 5/0022* (2013.01); *A61B 5/021* (2013.01); *A61B 5/7282* (2013.01); *A61B 5/0006* (2013.01); *A61B 5/0476* (2013.01); *A61B 5/1113* (2013.01); *A61B 5/746* (2013.01); *A61B 2560/0271* (2013.01); *A61B 2562/0219* (2013.01); *A61B 2562/08* (2013.01)

(58) Field of Classification Search
CPC ..... A61B 5/0205; A61B 5/002; A61B 5/0022; A61B 5/0024
USPC ....................................... 340/539.12
See application file for complete search history.

(56) References Cited

U.S. PATENT DOCUMENTS

| | | | |
|---|---|---|---|
| 2011/0061647 A1* | 3/2011 | Stahmann | A61B 5/0031 128/202.16 |
| 2015/0137621 A1* | 5/2015 | Emby | G05B 11/01 307/140 |
| 2018/0174686 A1* | 6/2018 | Zaphrir | G06F 3/011 |

FOREIGN PATENT DOCUMENTS

JP  2005-177342 A  7/2005

\* cited by examiner

*Primary Examiner* — Qutbuddin Ghulamali
(74) *Attorney, Agent, or Firm* — Sughrue Mion, PLLC (57) ABSTRACT

A patient monitoring system is provided. A sensor is attached to a subject. A processor acquires physiological information of the subject, and detects an occurrence of an event. A communication interface is wirelessly communicable with a remote device through a communication network. When the processor detects an occurrence of the event, a power supplying member supplies a first electric power that is necessary for transmission of physiological information to the remote device, to the communication interface. When an occurrence of the event is not detected, the power supplying member supplies a second electric power that is lower than the first electric power, to the communication interface.

6 Claims, 5 Drawing Sheets

SENSOR, AND PATIENT MONITORING SYSTEM

CROSS-REFERENCE TO RELATED APPLICATIONS

This application is based on and claims priority under 35 USC 119 from Japanese Patent Application No. 2018-112861 filed on Jun. 13, 2018, the contents of which are incorporated herein by reference.

TECHNICAL FIELD

The presently disclosed subject matter relates to a sensor which is attached to a subject and acquires physiological information of the subject, and also to a system which monitors the physiological information by using the sensor.

BACKGROUND ART

Patent Literature 1 discloses a patient monitoring system which includes a wireless telemeter and a central monitor. The central monitor is a device which is disposed in a nurse station or the like, and which centrally manages physiological information of a plurality of patients. Sensors which acquire physiological information are attached to the patients, respectively. The wireless telemeter transmits the physiological information which is acquired by the sensors, to the central monitor through wireless communication. The central monitor performs predetermined analysis and display processes on the received physiological information.

CITATION LIST

Patent Literature

[Patent Literature 1] JP-A-2005-177342

SUMMARY OF INVENTION

The system disclosed in Patent Literature 1 is configured on the assumption that a plurality of patient are always centrally monitored by the central monitor. Such a system tends to become large in scale, and its introduction is sometimes hardly performed. On the other hand, there is a request to provide a sensor itself which is attached to each of the patients, with a function of analyzing physiological information, and a wireless transmission function. In this case, a small battery or the like is used as an electric power source for driving the sensor, and therefore the power consumption due to the wireless communication cannot be negligible.

It is an object of the presently disclosed subject matter to provide a patient monitoring system in which the power consumption can be reduced, and which can be easily introduced.

A first aspect for achieving the object is a sensor that is attached to a subject, the sensor includes:
a processor which acquires physiological information of the subject, and which detects an occurrence of an event;
a communication interface which is communicable with a remote device through a communication network; and
a power supplying member which supplies a first electric power to the communication interface when the processor detects an occurrence of the event, the first electric power being necessary for transmission of physiological information to the remote device, and
wherein when an occurrence of the event is not detected, the power supplying member supplies a second electric power that is lower than the first electric power, to the communication interface.

A second aspect for achieving the object is a patient monitoring system, the system includes:
a sensor which is to be attached to a subject; and
a remote device,
the sensor includes:
a processor which acquires physiological information of the subject, and which detects an occurrence of an event;
a communication interface which is communicable with the remote device through a communication network; and
a power supplying member which supplies a first electric power to the communication interface when the processor detects the occurrence of the event, the first electric power being necessary for transmission of physiological information to the remote device,
wherein when an occurrence of the event is not detected, the power supplying member supplies a second electric power that is lower than the first electric power, to the communication interface.

According to the configuration, in the case where an occurrence of a predetermined event is not detected, the physiological information of the subject which is acquired by the sensor is not transmitted to the remote device. The electric power which is supplied from the power supplying member to the communication interface in the case where an occurrence of the event is not detected, is set to be lower than the electric power that is necessary for transmission of the physiological information. Even when the sensor is provided with a function of analyzing physiological information, and a wireless transmission function, therefore, the power consumption can be suppressed, and the monitoring environment can be provided for a longer period of time.

On the side of the remote device, on the other hand, physiological information transmitted from a specific subject is received under conditions that the event occurs. It is not necessary to always centrally monitor physiological information of a plurality of subjects, and therefore flexible remote monitoring in which a remote device such as a portable information terminal is used can be realized. As compared with a central monitor which is configured on the assumption that a plurality of patients are always centrally monitored, the patient monitoring system can be easily introduced.

DESCRIPTION OF EMBODIMENTS

Hereinafter, an embodiment will be described in detail with reference to the accompanying drawings. In the drawings, in order to make the components to be described, to have a recognizable size, their scales are appropriately changed.

Figure 1:
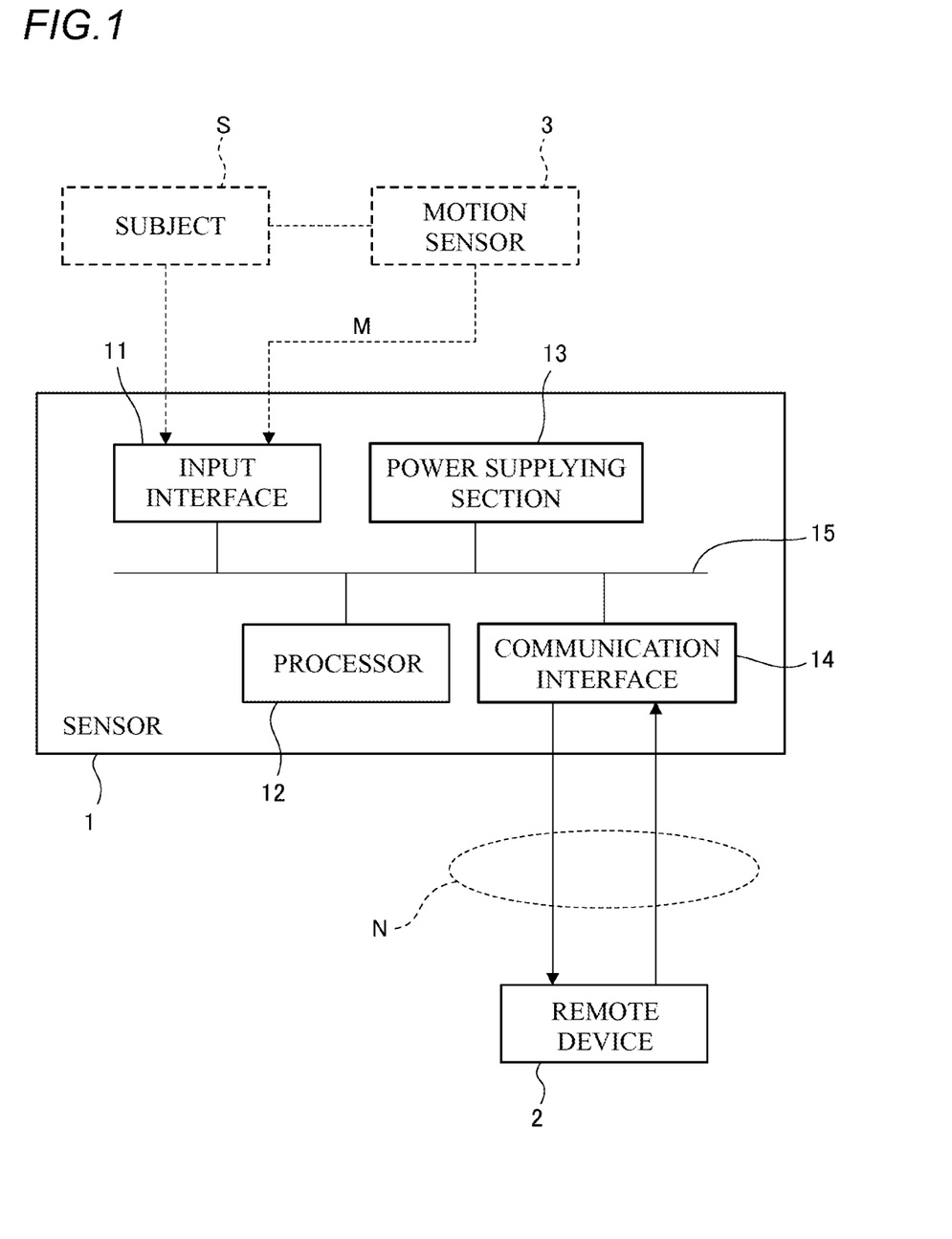
FIG. 1 illustrates the function configuration of a sensor of an embodiment.

FIG. 1 illustrates the function configuration of a sensor 1 of the embodiment. The sensor 1 is a device which is attached to the body of a subject S to acquire physiological information of the subject S. Examples of the physiological information are a value of a physiological parameter at least one a certain timing or a temporal change of the physiological parameter. Examples of the physiological parameter are an electrocardiogram, the pulse rate, the brain wave, the non-invasive arterial oxygen saturation (SpO2), the body temperature, the blood pressure, and the concentration or partial pressure of carbon dioxide contained in the respiratory gas.

At least one sensor 1 is attached to the subject S. Each sensor 1 may include a configuration in which at least one of the exemplified physiological parameters can be acquired. For example, a sensor for acquiring an electrocardiogram and the brain wave may include a plurality of electrodes which are to be attached to adequate body portions to detect biopotential of the portions. A sensor for acquiring the pulse rate and the SpO2 may include a light emitter and light receiver which are to be attached to the fingertip or the earlobe to detect the absorbance of the portion.

The sensor 1 may include an input interface 11, a processor 12, a power supplying member 13, a communication interface 14, and a bus 15. The bus 15 mutually connects the input interface 11, the processor 12, the power supplying member 13, and the communication interface 14 so as to enable data and signal exchange and power supply to be performed between these elements.

A signal corresponding to the state of the physiological parameter which is the detection target is supplied to the input interface 11. The input interface 11 may include an adequate circuit configuration for converting the supplied signal to data on which the processor 12 can execute a process that will be described later.

The processor 12 acquires physiological information of the subject S based on the data which are supplied through the input interface 11. The processor 12 has also a function of analyzing the acquired physiological information, and determining whether the subject S is in a normal condition or not. Based on acquired electrocardiogram information, for example, it is possible to determine whether the motion of the heart of the subject S is normal or not. Based on acquired blood pressure information, alternatively, it is possible to determine whether the blood pressure of the subject S is normal or not.

The power supplying member 13 is configured so as to be able to supply an electric power to the input interface 11, the processor 12, and the communication interface 14 via the bus 15. The power supplying member 13 may be realized by a primary battery, a secondary battery, or the like.

The communication interface 14 may include a configuration which can wirelessly communicate with a remote device 2 through a communication network N. The communication interface 14 may include a transmission circuit which can wirelessly transmit physiological information that is acquired by at least the processor 12, to the remote device 2. The remote device 2 may include a display which visualizes the physiological information that is received from the sensor 1. The communication interface 14 may further include a reception circuit which can wirelessly receive at least an inquiry signal that will be described later, from the remote device 2.

The communication network N may include at least one of: the PAN (Personal Area Network) which enables communication based on a standard such as the Bluetooth (registered trademark) or the NFC (Near Field Communication); the LAN (Local Area Network) which enables communication based on a standard such as the WiFi; and the WAN (Wide Area Network) which enables communication based on a standard such as the LTE (Long Term Evolution) or the LPWA (Low Power Wide Area). Therefore, each of the communication interface 14 and the remote device 2 may include transmission and reception circuits which are compliant with the standard that is used in wireless communication.

Figure 2:
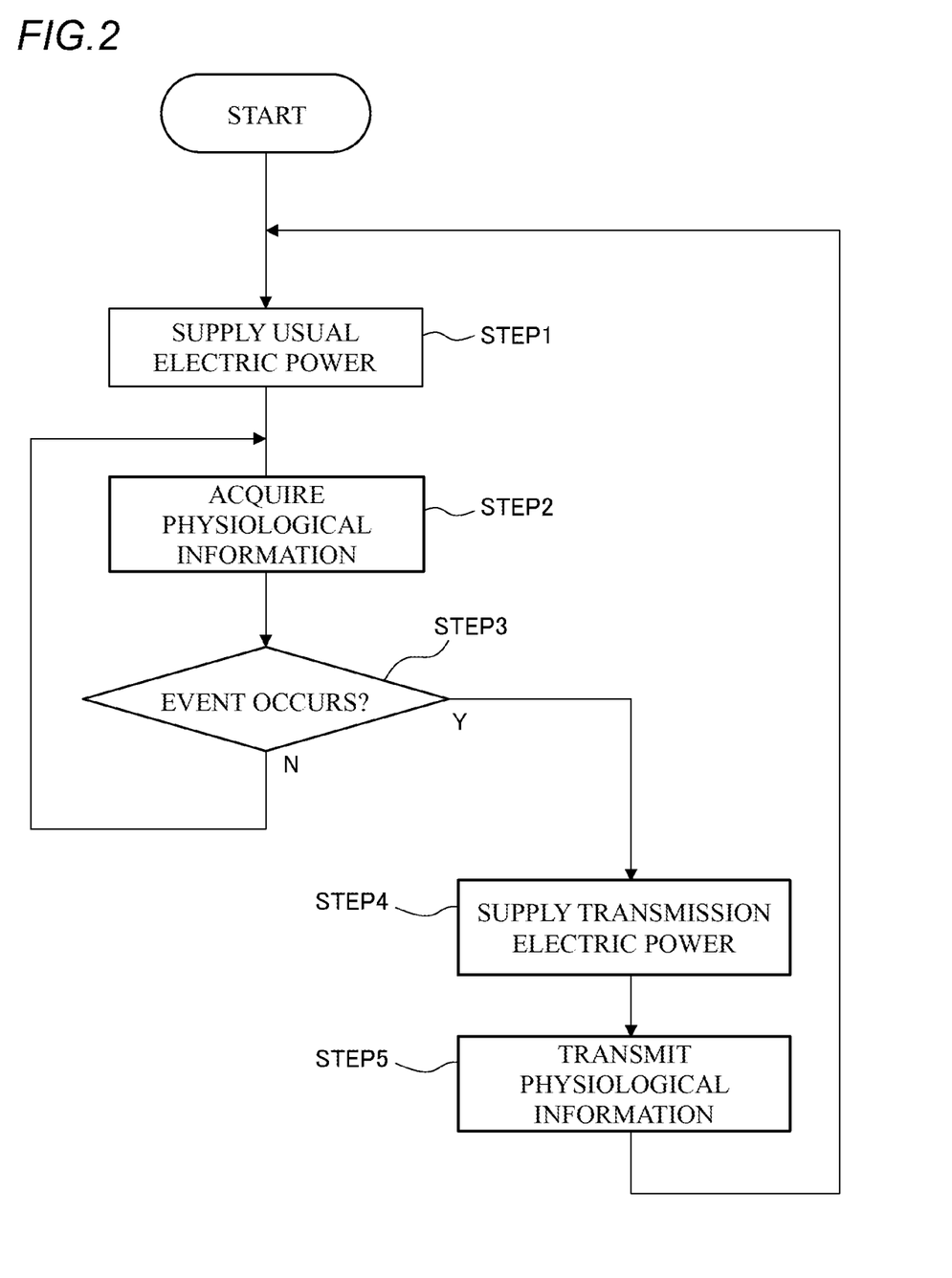
FIG. 2 illustrates the operation of the sensor.

FIG. 2 illustrates the operation of the thus configured sensor 1. When the sensor 1 is activated, the supply of a usual electric power from the power supplying member 13 to the input interface 11, the processor 12, and the communication interface 14 is started (STEP 1). An electric power which is required in the operation of the circuit for converting the supplied signal to data that can be processed by the processor 12 is supplied to the input interface 11. An electric power which is required in processes of acquiring and analyzing physiological information is supplied to the processor 12. Upon reception of the supply of the electric power, the processor 12 executes the processes of acquiring and analyzing physiological information (STEP 2).

An electric power which is lower than that necessary for transmission of the physiological information to the remote device 2 is supplied to the communication interface 14. More specifically, a standby electric power which allows the reception circuit to receive the signal transmitted from the remote device 2 is supplied to the reception circuit. The transmission electric power is an example of the first electric power, and the standby electric power is an example of the second electric power.

The processor 12 determines whether a predetermined event occurs or not (STEP 3). If it is determined that the event does not occur (N in STEP 3), the process returns to STEP 2, and the acquisition of physiological information by the processor 12 is continued. When the occurrence of the event is not detected, namely, the acquired physiological information is not transmitted to the remote device 2.

If it is determined that the predetermined event occurs (Y in STEP 3), the processor 12 causes the power supplying member 13 to supply the transmission electric power which is necessary for transmission of the physiological information by the transmission circuit, to the communication interface 14 (STEP 4). Upon reception of the supply of the transmission electric power, the communication interface 14 transmits the physiological information to the remote device 2 (STEP 5).

When the transmission of the physiological information is ended, the process returns to STEP 1, and the electric power which is supplied from the power supplying member 13 to the communication interface 14 is returned from the transmission electric power to the standby electric power.

Figure 3:
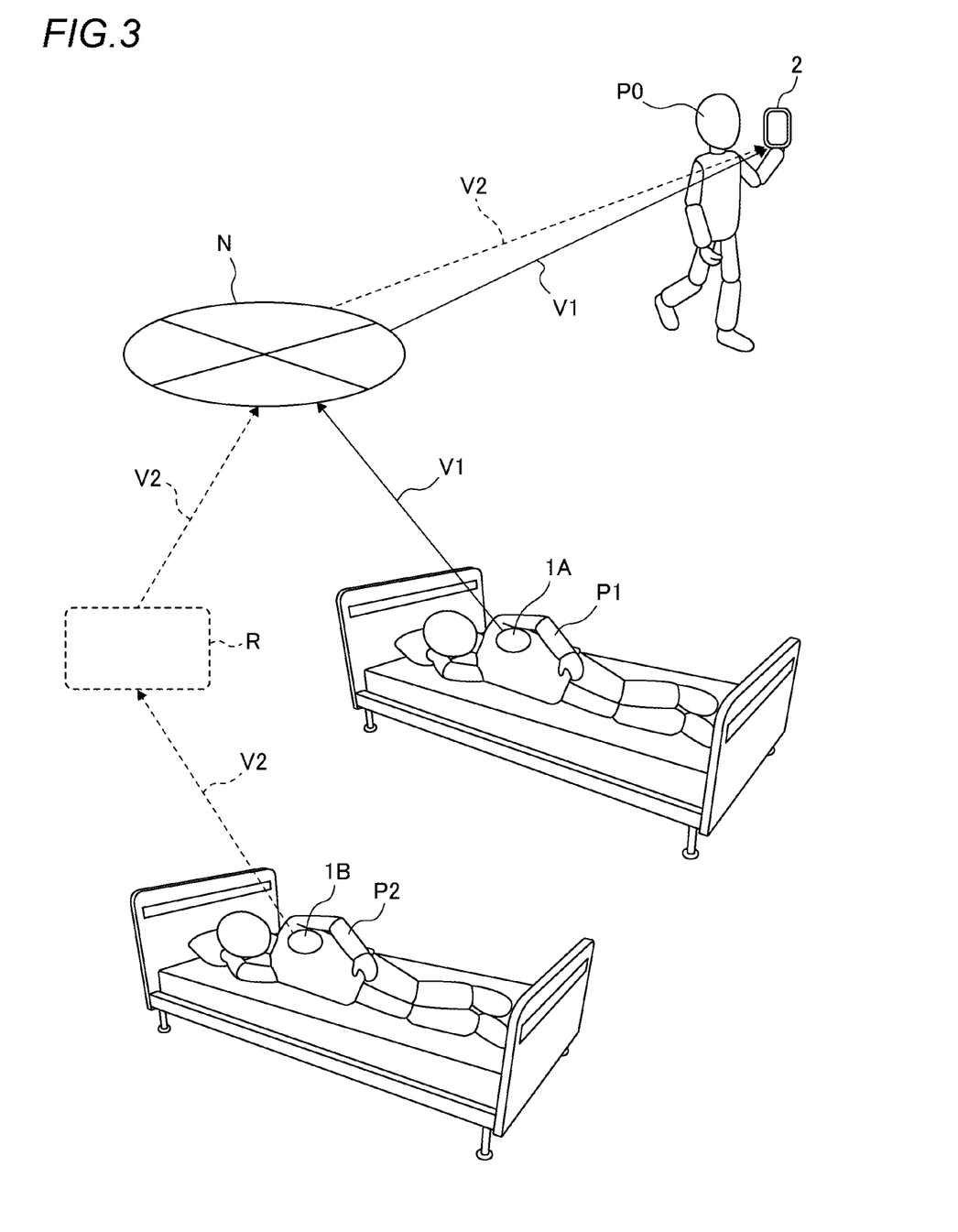
FIG. 3 illustrates an example of the operation of a patient monitoring system including the sensor.

The sensor 1 and remote device 2 which are configured as described above constitute the patient monitoring system. FIG. 3 illustrates an example of the operation of such a patient monitoring system. In the example, the physiological information of a first patient P1 and that of a second patient P2 are monitored by the remote device 2. Each of the first patient P1 and the second patient P2 is an example of the subject.

A sensor 1A is attached to the first patient P1. The sensor 1A has the configuration and function which are identical with those of the above-described sensor 1. A sensor 1B is attached to the second patient P2. The sensor 1B has the configuration and function which are identical with those of the above-described sensor 1. Although, in the illustrated example, one sensor is attached to each of the patients, a plurality of sensors may be attached to each of the patients. The number and type of the sensor(s) which is attached to each patient may be different depending on the patient.

The remote device 2 is placed in a place where an observer P0 such as a medical person can visually check the remote device. In the example, the remote device 2 is a device which can be carried by the observer P0. An example of such a device is a portable information terminal such as a smart phone or a tablet terminal.

The sensor may be configured so as to be able to be directly connected to the communication network N, or to be able to be connected to the communication network N through a relay device R. In the illustrated example, the sensor 1A can be connected to the communication network N based on a standard such as the LTE or the LPWA, and the sensor 1B can be connected to the communication network N through the relay device R. For example, the wireless communication between the sensor 1B and the relay device R may be performed based on a standard such as the Bluetooth (registered trademark), and that between the relay device R and the remote device 2 may be performed based on a standard such as the LTE or the LPWA.

In the illustrated example, an abnormal condition of the physiological information which is acquired from the first patient P1 is detected by the processor 12 of the sensor 1A. Examples of the abnormal condition of physiological information are listed below, but the abnormal condition is not limited to them:
- deviation of the heart rate from the normal value range;
- abnormality of an electrocardiogram waveform indicating ventricular fibrillation, ventricular tachycardia, etc.;
- abnormality of the brain wave indicating epilepsy, etc.;
- deviation of the blood pressure from the normal value range;
- deviation of the body temperature from the normal value range;
- deviation of the SpO2 from the normal value range;
- deviation of the concentration or partial pressure of carbon dioxide contained in the respiratory gas, from the normal value range;
- abnormality of the respiratory gas waveform indicating airway narrowing, etc.; and
- waveform abnormality which may be caused by a displacement from the attachment position of the sensor, slipping off or failure of the sensor, or noise mixing.

The detection of an abnormal condition of physiological information is an example of the above-described event. In the sensor 1A, therefore, the transmission electric power is supplied from the power supplying member 13 to the communication interface 14. Then, the communication interface 14 transmits physiological information V1 which is acquired by the processor 12, to the remote device 2.

The remote device 2 receives the physiological information V1 which is transmitted from the sensor 1A. The physiological information V1 is visualized on the display of the remote device 2. The observer P0 recognizes the abnormal condition of the physiological information of the first patient P1 through the display, and takes necessary measures.

On the other hand, the processor 12 of the sensor 1B does not detect an abnormal condition of the physiological information which is acquired from the second patient P2. In the sensor 1B, therefore, the standby electric power is supplied from the power supplying member 13 to the communication interface 14. Consequently, the physiological information of the second patient P2 is not transmitted from the sensor 1B to the remote device 2. When an abnormal condition of the physiological information which is acquired from the second patient P2 is detected by the processor 12 of the sensor 1B, physiological information V2 is transmitted from the sensor 1B to the remote device 2 through the relay device R as indicated by the broken lines in FIG. 3.

Figure 4:
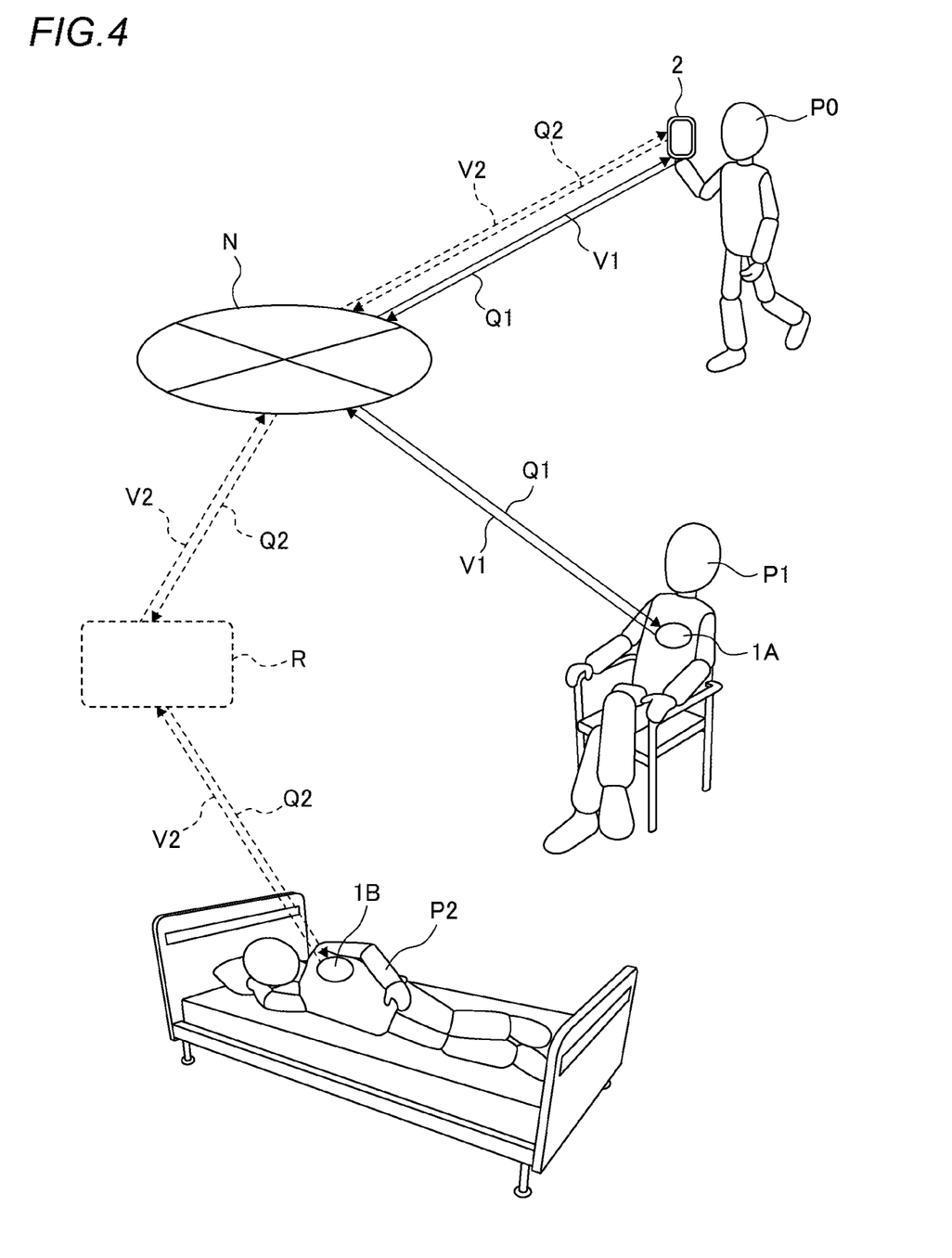
FIG. 4 illustrates another example of the operation of the patient monitoring system including the sensor.

FIG. 4 illustrates another example of the operation of the patient monitoring system. In the example, the case where the observer P0 wishes to remotely check the physiological information of the first patient P1 will be described.

The observer P0 inputs a predetermined operation to the remote device 2 to cause the inquiry signal Q1 to be transmitted to the sensor 1A which is attached to the first patient P1. When the inquiry signal Q1 is received by the communication interface 14 of the sensor 1A, the usual electric power is supplied from the power supplying member 13 to the communication interface 14. Namely, the reception in which the inquiry is transmitted from the remote device 2 is received by the communication interface 14 is an example of the above-described event.

Therefore, the communication interface 14 transmits the physiological information V1 which is acquired by the processor 12, to the remote device 2. The remote device 2 receives the physiological information V1 which is transmitted from the sensor 1A. The physiological information V1 is visualized on the display of the remote device 2. The observer P0 can remotely check the physiological information of the first patient P1 through the display.

On the other hand, the communication interface 14 of the sensor 1B which is attached to the second patient P2 does not receive the inquiry signal that is transmitted from the remote device 2. In the sensor 1B, therefore, the standby electric power is supplied from the power supplying member 13 to the communication interface 14. Consequently, the physiological information of the second patient P2 is not transmitted from the sensor 1B to the remote device 2.

When, as indicated by the broken lines in FIG. 4, the observer P0 then causes the remote device 2 to transmit an inquiry signal Q2 to the sensor 1B, and the inquiry signal Q2 is received by the communication interface 14 of the sensor 1B, the electric power which is supplied from the power supplying member 13 to the communication interface 14 is switched from the standby electric power to the transmission electric power. Therefore, the physiological information V2 is transmitted from the sensor 1B to the remote device 2. In the sensor 1A which is attached to the first patient P1, during this period, the electric power which is supplied from the power supplying member 13 to the communication interface 14 is switched from the transmission electric power to the standby electric power. Therefore, the physiological information of the first patient P1 is not transmitted from the sensor 1A to the remote device 2.

Figure 5:
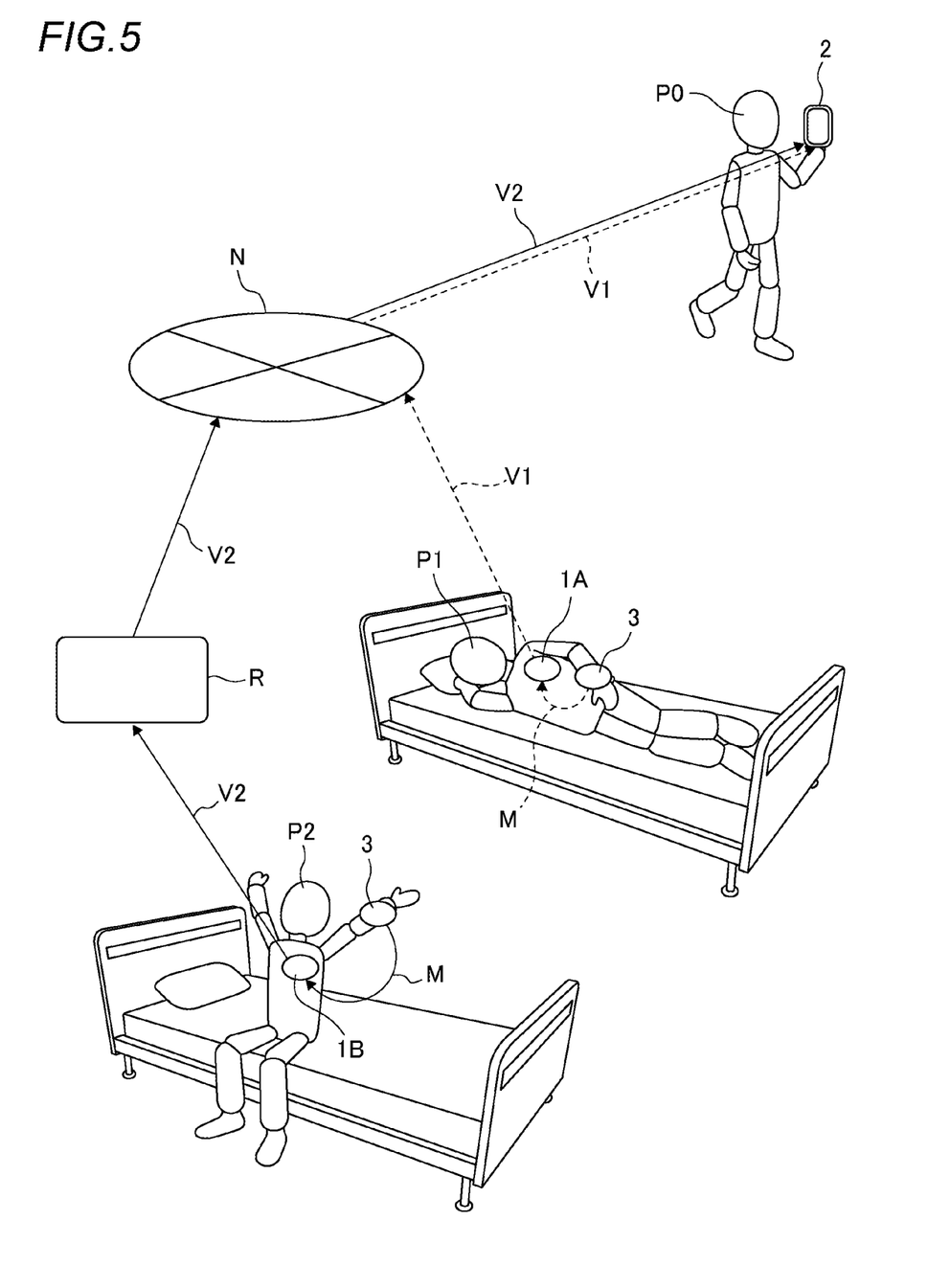
FIG. 5 illustrates a further example of the operation of the patient monitoring system including the sensor.

FIG. 5 illustrates a further example of the operation of the patient monitoring system. In the example, a motion sensor 3 is attached to the first patient P1 in addition to the sensor 1A. In the same or similar manner, another motion sensor 3 is attached to the second patient P2 in addition to the sensor 1B. Each of the motion sensors 3 detects the motion of an object to which the sensor is attached, and may be realized by an acceleration sensor or a gyroscope sensor. Alternatively, the motion sensors 3 may be incorporated in the sensors 1A, 1B, respectively.

As illustrated in FIG. 1, each of the motion sensors 3 is configured so that the sensor is attached to the subject S, and outputs a signal M corresponding to the body motion of the subject S. The signal M is supplied to the corresponding input interface 11. In this case, the input interface 11 may include an adequate circuit configuration for converting the signal M to data on which the processor 12 can execute a process. The processor 12 is configured so as to determine whether the motion of the subject S is normal or not, based on data corresponding to the signal M.

In the example illustrated in FIG. 5, an abnormal motion of the second patient P2 is detected by the motion sensor 2 attached to the second patient P2. Examples of an abnormal motion are abnormal wakefulness during sleeping time, and wandering. The detection of an abnormal motion of the subject is an example of the above-described event. In the sensor 1B, therefore, the transmission electric power is supplied from the power supplying member 13 to the communication interface 14. Consequently, the communication interface 14 transmits the physiological information V2 which is acquired by the processor 12, to the remote device 2.

The remote device 2 receives the physiological information V2 which is transmitted from the sensor 1B. The physiological information V2 is visualized on the display of the remote device 2. The observer P0 recognizes the abnormal motion of the second patient P2 through the display, and takes necessary measures.

On the other hand, the processor 12 of the sensor 1A does not detect an abnormal motion of the first patient P1. In the sensor 1A, therefore, the standby electric power is supplied from the power supplying member 13 to the communication interface 14. Consequently, the physiological information of the first patient P1 is not transmitted from the sensor 1A to the remote device 2. When an abnormal condition of the physiological information which is acquired from the second patient P2 is detected by the processor 12 of the sensor 1A, the physiological information V1 is transmitted from the sensor 1A to the remote device 2 as indicated by the broken lines in FIG. 5.

As described above, when an occurrence of a predetermined event is not detected, the physiological information of the subject S which is acquired by the sensor 1 is not transmitted to the remote device 2. The electric power which is supplied from the power supplying member 13 to the communication interface 14 in the case where an occurrence of the event is not detected is set to be lower than the electric power that is necessary for transmission of the physiological information. Even when the sensor 1 is provided with a function of analyzing physiological information, and a wireless transmission function, therefore, the power consumption can be suppressed, and the monitoring environment can be provided for a longer period of time.

On the side of the remote device 2, by contrast, physiological information transmitted from a specific subject S is received under conditions that the event occurs. It is not necessary to always centrally monitor physiological information of a plurality of subjects, and therefore flexible remote monitoring in which the remote device 2 such as a portable information terminal is used can be realized. As compared with a central monitor which is configured on the assumption that a plurality of patients are always centrally monitored, the patient monitoring system can be easily introduced.

The above-described function of the processor 12 may be realized by a general-purpose microprocessor which operates in cooperation with a memory, or by a dedicated integrated circuit such as a microcomputer, an ASIC, or an FPGA.

The above-described embodiment is a mere example for facilitating understanding of the disclosure. The configuration of the embodiment may be adequately changed or improved without departing from the spirit of the presently disclosed subject matter.

In the example illustrated in FIG. 4, the process is started when the observer P0 spontaneously causes the remote device 2 to transmit the inquiry signal. In response to the transmission in which physiological information is transmitted from the sensor as illustrated in FIGS. 3 and 5, however, the observer P0 may cause the remote device 2 to transmit the inquiry signal. In the case where the transmission of physiological information from the sensor is temporary, for example, the observer P0 may request, in order to check the cause of the transmission, the remote device 2 to retransmit physiological information. The retransmitted physiological information may be subjected to visual diagnosis which is performed by the observer P0 through the display of the remote device 2, or during a predetermined time period to an analysis process which is performed by a processor incorporated in the remote device 2, and which is equivalent to that in the processor 12 of the sensor 1. In the latter case, the physiological information is doubly analyzed, and therefore the accuracy of the decision can be improved.

In the case where the function in which the sensor 1 replies to the inquiry from the remote device 2 as illustrated in FIG. 4 is not necessary, the reception circuit can be omitted in the communication interface 14. In this case, the usual electric power which is supplied from the power supplying member 13 to the communication interface 14 when an occurrence of an event is not detected may be set to a level which is minimally required for maintaining the standby state of the transmission circuit. This electric power may be zero.

What is claimed is:

1. A sensor that is attached to a subject, the sensor comprising:
    a processor which acquires physiological information of the subject and which detects an occurrence of an event;
    a communication interface which is wirelessly communicable with a remote device through a communication network; and
    a power supplying member which supplies electric power to the communication interface,
    wherein when the processor detects an occurrence of the event, the processor controls the power supplying member to supply to the communication interface a first electric power being necessary for the communication interface to perform transmission of physiological information to the remote device,
    wherein when the occurrence of the event is not detected, the processor controls the power supplying member to supply to the communication interface a second electric power that is lower than the first electric power.

2. The sensor according to claim 1, wherein the event is a detection of an abnormal condition of the physiological information by the processor.

3. The sensor according to claim 1, wherein the event is an inquiry from the remote device which is received by the communication interface.

4. The sensor according to claim 1, wherein the communication interface is communicable with a motion sensor which is attached to the subject, and the event is a detection of an abnormal motion of the subject by the motion sensor.

5. A patient monitoring system comprising:
    a sensor which is attached to a subject; and a remote device, the sensor includes:
- a processor which acquires physiological information of the subject and which detects an occurrence of an event;
- a communication interface which is communicable with the remote device through a communication network; and
- a power supplying member which supplies electric power to the communication interface, wherein when the processor detects the occurrence of the event, the processor controls the power supplying member to supply to the communication interface a first electric power being necessary for the communication interface to perform transmission of physiological information to the remote device, and wherein when the occurrence of the event is not detected, the processor controls the power supplying member to supply to the communication interface a second electric power that is lower than the first electric power.

6. The patient monitoring system according to claim 5, wherein the remote device is a portable device.

\* \* \* \* \*